United States Patent [19]
White

[11] Patent Number: 5,623,762
[45] Date of Patent: Apr. 29, 1997

[54] HYPODERMIC NEEDLE DISPOSAL APPARATUS

[76] Inventor: Jennifer A. White, 53 Putnam Ave., Cambridge, Mass. 02138

[21] Appl. No.: 291,799

[22] Filed: Aug. 17, 1994

[51] Int. Cl.$^6$ ............................................ B23P 19/00
[52] U.S. Cl. .......................... 29/816; 29/280; 29/283.5; 29/818
[58] Field of Search ......................... 29/278, 280, 283.5, 29/809, 811.2, 816, 817, 818

[56] References Cited

U.S. PATENT DOCUMENTS

| | | | |
|---|---|---|---|
| 3,599,472 | 8/1971 | Koletsos | 29/818 X |
| 4,160,317 | 7/1979 | Sergeant | 29/816 X |
| 4,173,067 | 11/1979 | Steiner et al. | 29/816 X |
| 4,953,384 | 9/1990 | Baillet et al. | 29/816 X |
| 5,392,509 | 2/1995 | Cheswick | 29/818 |

*Primary Examiner*—S. Thomas Hughes
*Attorney, Agent, or Firm*—John E. Toupal; Harold G. Jarcho

[57] ABSTRACT

A ferrule applying device including first and second jaws defining an engagement chamber and reciprocably movable with respect to each other into and out of said engagement chamber, a retainer for retaining a plurality of ferrules, and a feed mechanism for automatically and sequentially feeding individual ferrules from the retainer into a given position within the engagement chamber. Also included is an entry passage shaped and arranged to allow insertion of a shaft into a ferrule positioned in the engagement chamber, and an actuator for producing relative closure movement between the first and second jaws into engagement with the ferrule so as to cause crimping thereof on the shaft.

19 Claims, 5 Drawing Sheets

HYPODERMIC NEEDLE DISPOSAL APPARATUS

BACKGROUND OF THE INVENTION

This invention relates generally to a method and apparatus for use in disposing of hypodermic needles and more specifically, to such a method and apparatus that prevents inadvertent punctures with contaminated needles.

Among the most frequently reported healthcare personnel injury in hospitals is accidental needlesticks. Accidental needlesticks commonly occur when the sharp portion of a hypodermic needle unintentionally enters the skin of the healthcare personnel following the needle's use on a patient. Serious blood borne diseases including AIDS or hepatitis B can be transmitted to the healthcare personnel through an accidental needlestick following a hypodermic needle's use on an infected patient. The period of greatest risk for serious accidental needlestick injuries occurs after a patient's blood is drawn and before the hypodermic needle is discarded. Proper disposal of a used hypodermic needle usually ends by discarding the needle into a hard-walled plastic container. Prior to discarding the hypodermic needle, it may be recapped, broken, or removed from its attachment site on the syringe or blood-drawing apparatus. Needlestick injuries commonly occur to the healthcare personnel while they are performing these tasks. When used needles are disposed of improperly, hospital maintenance and laundry staff are also at risk of sustaining needlestick injuries.

Because of the serious risk of inadvertent needle-punctures, there is a clear need to improve the process of disposing of used needles such that the risk of disease transmission attributed to accidental needlestick injuries to healthcare personnel is reduced. Various attempts to reduce the risk of needlestick injuries have focussed on either redesigning needle caps or adding recapping apparatus. Other attempts to alleviate the problem have focussed on redesigning the syringe itself. The disadvantages of these approaches are that they are complex and expensive to manufacture. They are also limited in their function with the wide variety of needle apparatus types and sizes.

The object of this invention, therefore, is to provide an improved method and apparatus for use in disposing of used hypodermic needles.

SUMMARY OF THE INVENTION

The invention is a ferrule applying device including first and second jaws defining an engagement chamber and reciprocably movable with respect to each other into and out of said engagement chamber, a retainer for retaining a plurality of ferrules, and a feed mechanism for automatically and sequentially feeding individual ferrules from the retainer into a given position within the engagement chamber. Also included is an entry passage shaped and arranged to allow insertion of a shaft into a ferrule positioned in the engagement chamber, and an actuator for producing relative closure movement between the first and second jaws into engagement with the ferrule so as to cause crimping thereof on the shaft. The device simplifies the crimping of a ferrule on a shaft such as a hypodermic needle.

According to features of the invention the first and second jaws experience relative pivotal movement into and out of the engagement chamber; the device includes means biasing the jaws out of the engagement cavity; the actuator comprises a first arm extending from the first jaw and a second arm extending from the second jaw, the first and second arms being adapted for manual actuation to produce the relative pivotal movement of the Jaws into the engagement chamber. The arms and pivotal movement facilitate manual activation of the jaws during a crimping operation.

According to other features of the invention, the retainer includes a housing shaped and arranged to retain the ferrules in parallel engaged alignment within an elongated row having one end directly adjacent to the engagement chamber and an opposite end substantially spaced therefrom, the feed mechanism applies to the ferrule row a force directed toward the engagement chamber, and the first and second jaws define an abutment for engaging the individual ferrule within the engagement chamber so as to oppose the force induced by the feed mechanism. This structural arrangement insures sequential feeding and positioning of individual ferrules in the engagement chamber.

According to yet other features of the invention, the device includes a stop for limiting relative movement of the jaws in response to squeezing of the arms, and the retainer consists of a cartridge removably retained by the first arm, and the feed mechanism includes a spring exerting the force against the row of ferrules. The stop establishes a predetermined degree of crimping and the removable cartridge simplifies repeated loading of the device with ferrules.

According to still other features of the invention, the cartridge defines an engagement cavity disposed within the engagement chamber, an opening into the engagement cavity, and the abutment that projects into the engagement cavity; the second jaw defines a contact wedge portion adapted to enter the chamber through the opening and engage the individual ferrule therein, the contact wedge having an axis extending transversely to the individual ferrule and substantially aligned with the mid-portion thereof; and the cartridge further defines a wedge shaped recess disposed in the engagement cavity opposite to the opening and having an axis substantially parallel to the axis of the contact wedge. These features facilitate proper crimping of the ferrule between the contact wedge and the wedge shaded recess.

According to an important feature of the invention, the abutment is aligned with the mid-portion of the ferrule and extends in a direction parallel thereto a distance substantially less than the length of the ferrule so as to accommodate passage of the crimped portion of the ferrule out of the engagement cavity. This structural arrangement facilitates removal of the crimped ferrule and prevents jamming of ferrules in the engagement cavity.

According to other important features of the invention, the first jaw further defines the entry passage which is axially aligned with the individual ferrule in the engagement cavity; and an exit passage communicating with a portion of the engagement chamber separated from the engagement cavity by the abutment. The exit passage permits removal of the crimped together shaft and ferrule from the engagement chamber.

According to additional features of the invention, the entry passage is defined by a funnel having an inner end with dimensions smaller than those of the exit passage, and the cartridge further defines a ramp portion adapted to guide movement of the crimped together shaft and ferrule through the exit passage. The smaller entry passage guides movement of the shaft into the ferrule, the larger exit passage permits removal of the crimped ferrule, and the ramp guides movement of the ferrule through the exit passage.

The invention also encompasses a method for preparing hypodermic needles for disposal and including the steps of inserting the tip of a hypodermic needle into an open end of a ferrule; positioning the ferrule and needle between a pair of jaws movable with respect to each other; and moving the jaws into engagement with the ferrule so as to produce crimping together of the ferrule and the needle so as to prevent removal thereof from the ferrule. The crimped ferrule covers the point of the needle so as to prevent inadvertent punctures thereby.

According to a feature of the above method, an end of the ferrule opposite to the open end is closed. The closed ferrule end further protects against inadvertent physical contact with the needle.

DESCRIPTION OF THE DRAWINGS

These and other objects and features of the invention will become more apparent upon a perusal of the following description taken in conjunction with the accompanying drawings wherein:

FIG. 8 is a perspective view illustrating actuation of the device on an inserted needle;

FIG. 12 is a perspective view illustrating removal of a crimped together ferrule and needle from the device.

DESCRIPTION OF THE PREFERRED EMBODIMENT

Figure 1:
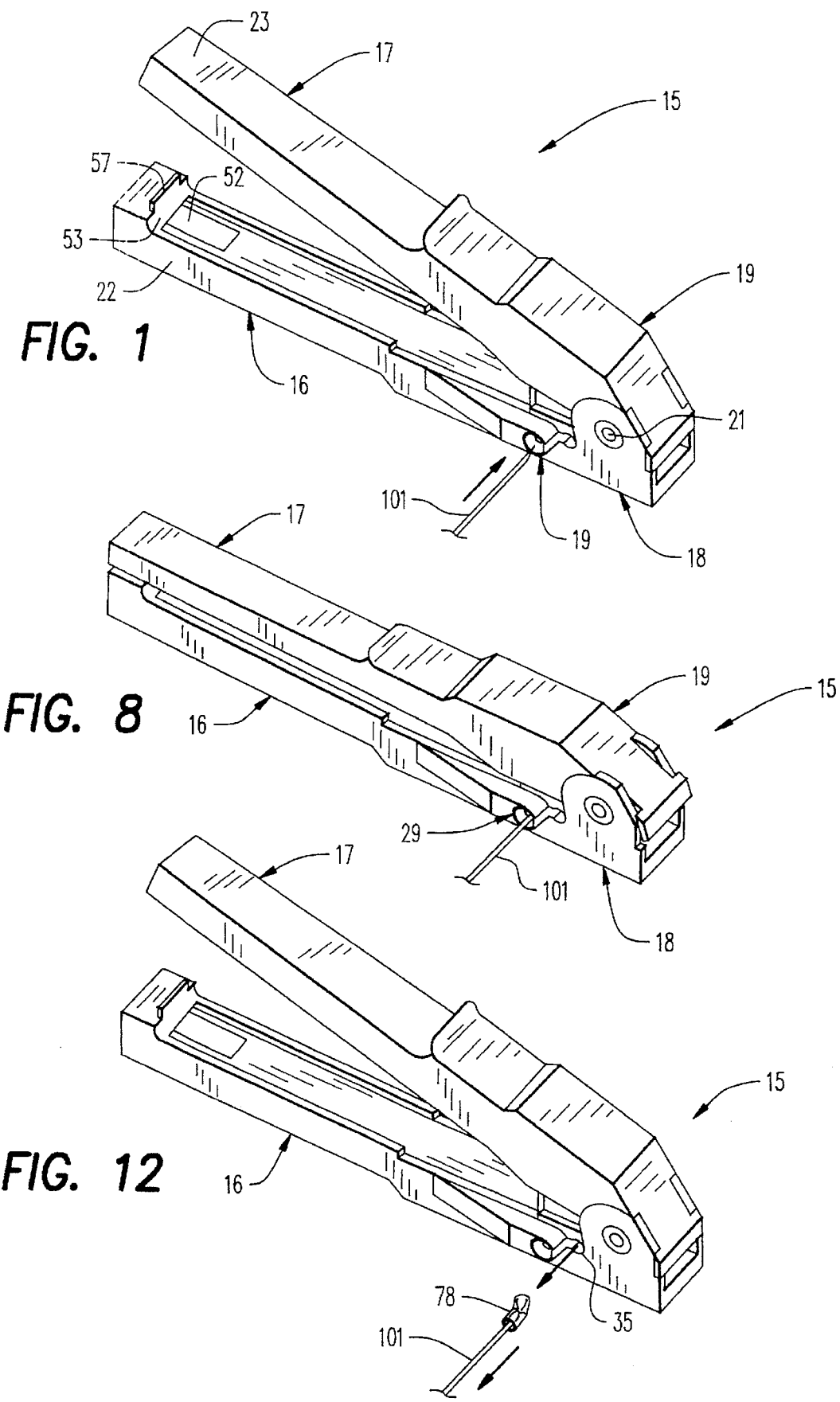
FIG. 1 is a perspective view of a device for use in safely disposing of hypodermic needles.

A portable, hand operated device 15 for use in safely disposing of hypodermic needles includes first and second actuator arms 16, 17. Terminating one end of the first arm 16 is a first jaw portion 18 while a second jaw portion 19 terminates one end of the second arm 17. The first and second jaw portions 18, 19 are attached for pivotal movement by a pivot pin 21. Opposite ends 22, 23 of the arms 16, 17, respectively, are adapted to be gripped by hand and squeezed to induce pivotal closure movement of the jaw portions 18, 19 in a manner described hereinafter.

Figure 2:
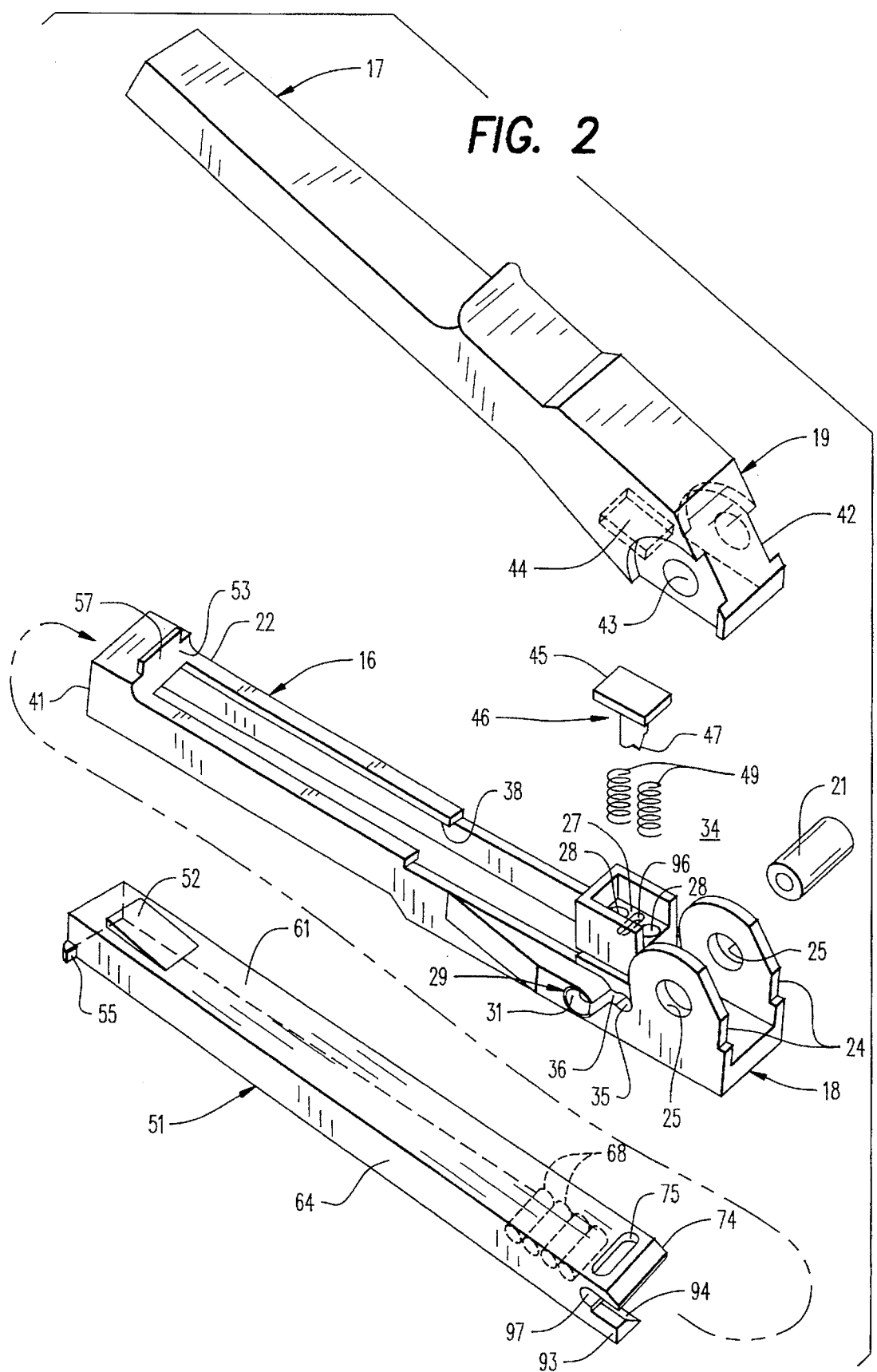
FIG. 2 is an exploded perspective view of the device shown in FIG. 1.

The first jaw portion 18 includes a pair of spaced apart legs 24 with apertures 25 that receive the pivot pin 21 as shown in FIG. 2. Also included in the first jaw portion 18 is an upwardly opening enclosure 26 with a bottom wall 27 that defines a pair of circular recesses 28. Projecting outwardly from one side of the first jaw portion 18 is a funnel portion 29 having an outer opening 31, a smaller inner opening 32 and a longitudinal removal passage or slot 30 extending therebetween. The inner opening 32 defines an entry passage into an engagement chamber 34 disposed between the first and second jaw portions 18, 19. An exit passage 35 substantially larger than the entry passage 32 extends through one of the legs 24 and communicates with the entry passage 32 via a removal passage or slot 36. Formed by the first actuator arm 16 is an elongated slot 38 having an outer open end 41 and a inner end communicating with the engagement chamber 34 between the first and second jaw portions 18, 19.

The second jaw portion 19 includes a spindle portion 42 (FIG. 2) that is retained between the legs 24 of the first jaw portion 18 and defines a bore 43 that accommodates sliding movement of a suitably dimensioned head portion 45 of an insert 46. A contact wedge portion 47 of the insert 46 extends downwardly from the head portion 45. Retained by the circular recesses 28 in the bottom wall 27 of the enclosure 26 are a pair of bias spring members 49 that engage and force the head portion 45 of the insert 46 against an inner surface of the recess 44. The bias spring members 49 bias the first and second arms 16, 17 in an open position shown in FIG. 1.

A retainer housing in the form of a cartridge 51 is removably retained by the elongated slot 38 in the first arm 16 as shown in FIG. 2. The cartridge 51 is inserted into the open end 41 of the first arm 16 and is retained in the slot 38 by engagement between an upwardly projecting tab 52 on the cartridge 51 and an upwardly projecting inwardly facing surface 53 on the end 22 of the arm 16. Inward penetration of the cartridge 51 within the slot 38 is limited by engagement between transversely extending shoulder portions 55 that engage the outer end 41 of the first arm 16. Extending upwardly from the end 22 of the arm 16 is a ridge stop 57, the function of which is described hereinafter.

Figure 3:
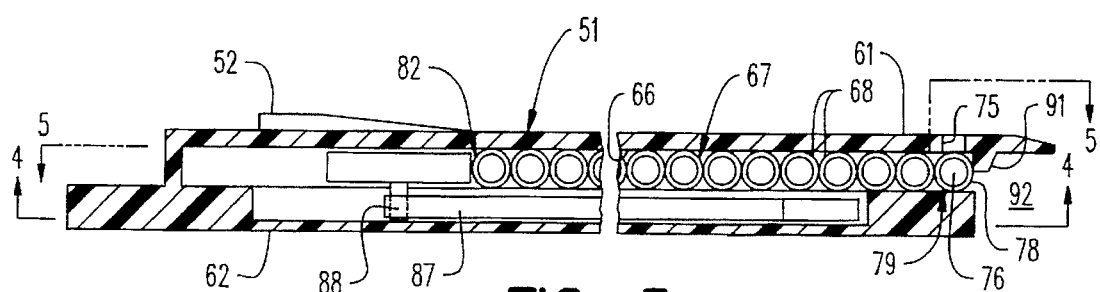
FIG. 3 is a cross sectional view of a ferrule retaining cartridge utilized in the device shown in FIGS. 1 and 2.
Figure 4:
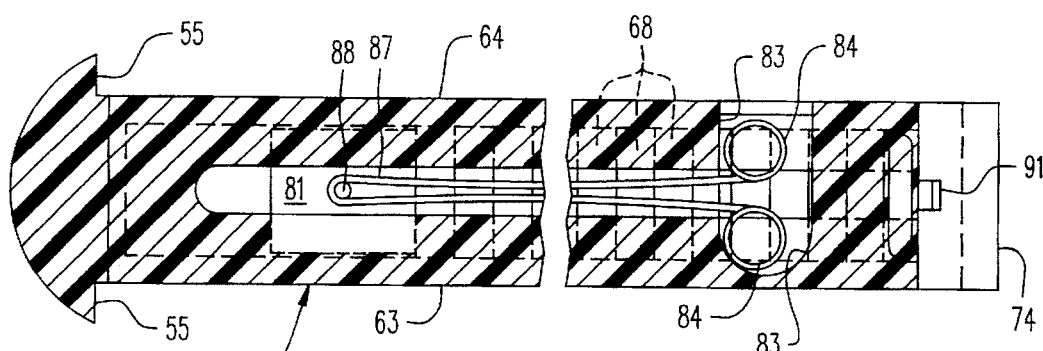
FIG. 4 is a cross sectional view taken along lines 4—4 of FIG. 3.
Figure 5:
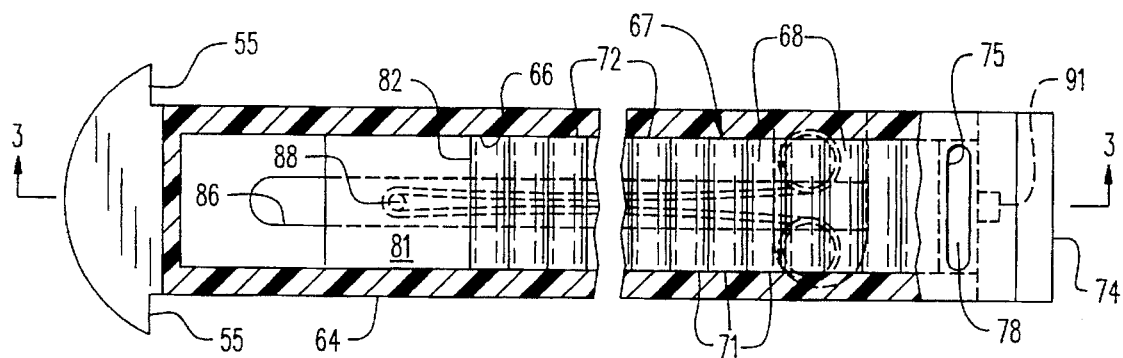
FIG. 5 is a cross sectional view taken along lines 5—5 of FIG. 3.

As shown in FIGS. 3–5, the cartridge 51 includes a top wall 61, a bottom wall 62 and sidewalls 63, 64. Defined by the walls 61–64 is an elongated housing 66 that retains a row 67 of parallel, engaged ferrules 68 having open ends 71 all facing in one direction and closed ends 72 facing the opposite direction. An inner end 74 of the top wall 62 defines an upwardly facing opening 75 that communicates with an engagement cavity 76 disposed between the top wall 61 and the bottom wall 62. Retained within the engagement cavity 76, is an individual ferrule 78 located at one end of the ferrule row 67. A block 81 is retained in the elongated housing 66 and engages an opposite end 82 of the ferrule row 67. Retained within recesses 83 in the bottom wall 62 are coiled end portions 84 of a feed spring 85. An elongated slot 86 in the bottom wall 62 communicating with the slots 83 retains an elongated mid-portion 87 of the spring 85. Encircled by the mid-spring portion 87 is a pin 88 that is secured to the block 81.

Also defined by the cartridge 51 is an abutment 91 that projects downwardly from the top wall 61 adjacent to the outer end of the engagement cavity 76. As shown in FIGS. 4 and 5, the abutment 91 extends a distance parallel to the axis of the ferrule 78 that is substantially shorter than the length thereof and is disposed in alignment with a mid-portion thereof. The spring member 85 exerts on the block 81 a force that pushes the ferrule row 67 into a position wherein the end individual ferrule 78 is retained within the engagement cavity 76 by engagement with the abutment 91. A removal cavity 92 communicating with the engagement cavity 76 but separated therefrom by the abutment 91 is formed at the inner end of the cartridge 51. An inwardly extending stem 93 (FIG. 2) at the inner end of the bottom wall 62 forms an upwardly sloping ramp 94 extending between the removal cavity 92 and the exit passage 35 in the first jaw portion 18.

OPERATION

Prior to use of the device 15, the cartridge 51 is inserted into the open end 41 of the first arm 16 until the shoulder portions 55 engage the outer end 41 and the tab 52 engages the upwardly extending surface 53. With the cartridge in that position, the engagement cavity 76 is located within the engagement chamber 34 between the first and second jaws 18, 19 and an orifice 96 in the bottom wall 27 of the enclosure 26 communicates with the opening 75 in the top wall 61. Also, the entry passage 32 of the funnel 29 is aligned with an entry opening 97 (FIG. 7) in the sidewall 64 of the cartridge 51 and extending transversely into the removal cavity 92. Preferably, the cartridge 51 is a preloaded disposable unit that is replaced after exhaustion of all ferrules 68 retained within the housing 66.

Figure 6:
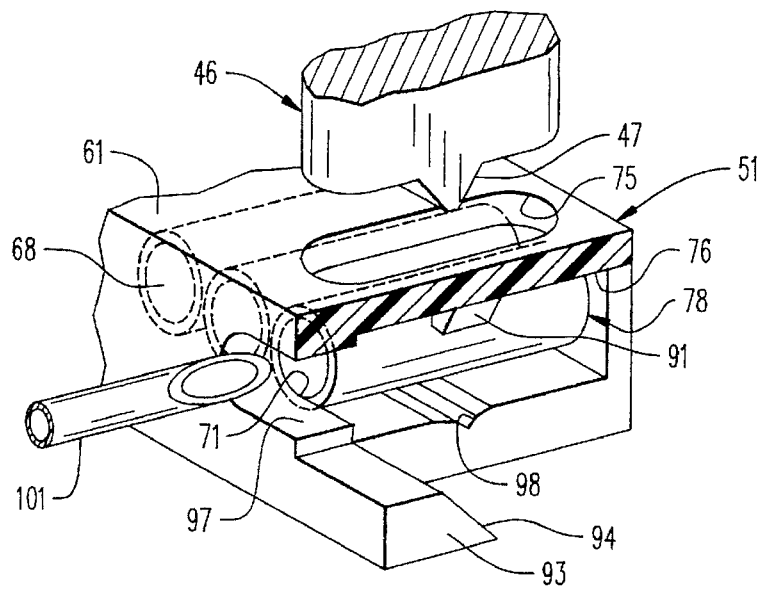
FIG. 6 is a perspective view illustrating entry of a hypodermic needle into the device shown in FIG. 1.
Figure 9:
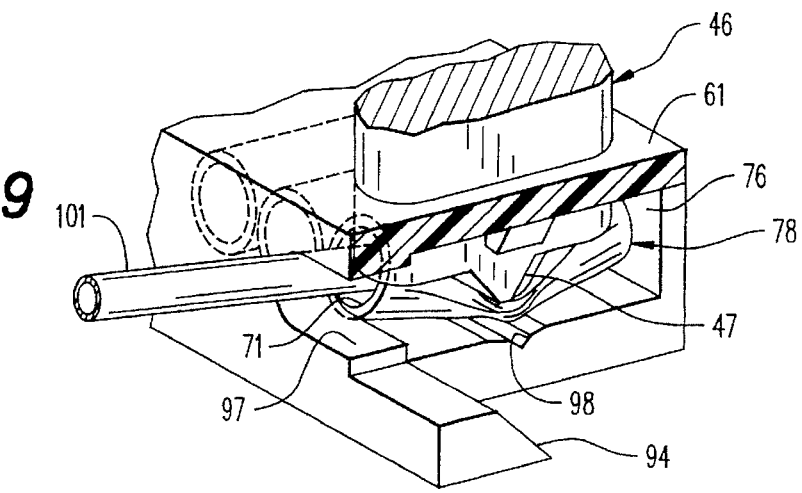
FIG. 9 is a perspective view illustrating crimping of a ferrule on an inserted needle.
Figure 7:
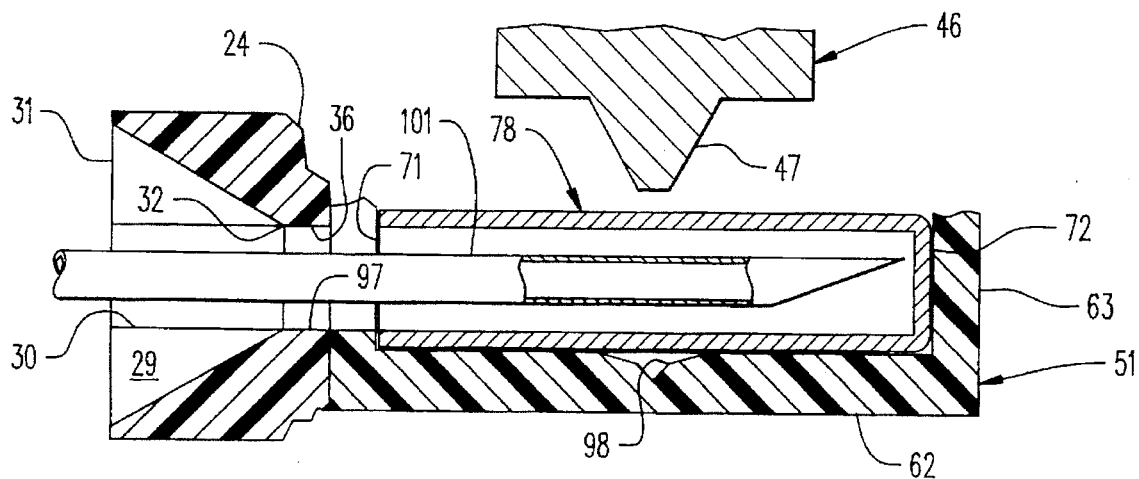
FIG. 7 is a cross sectional view illustrating a hypodermic needle disposed within the device shown in FIG. 1.
Figure 10:
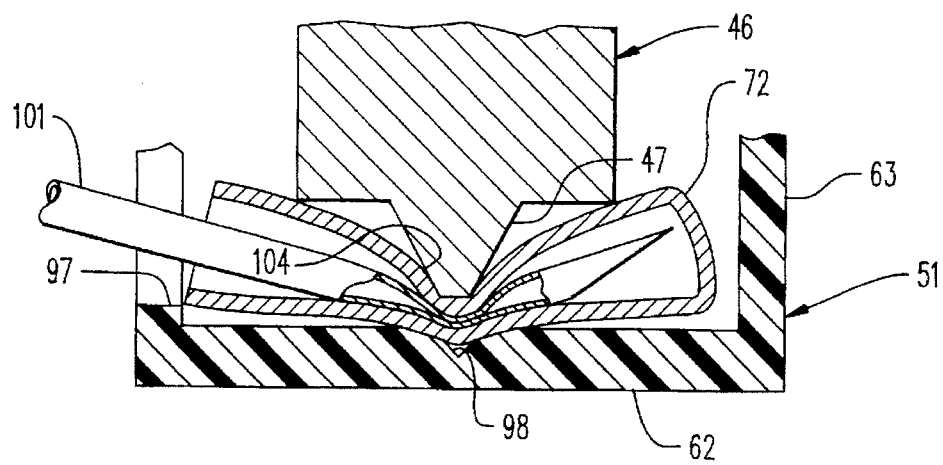
FIG. 10 is a cross sectional view illustrating crimping of the ferrule on a needle.

After loading of the device 15, a used hypodermic needle 101 is prepared for disposal by being inserted into the funnel 29 portion of the first jaw 18 as shown in FIGS. 1 and 6. The larger opening 31 of the funnel 29 facilitates access of the needle 101 while the smaller inner entry passage 32 thereof insures proper axial alignment of the needle 101 within the end ferrule 78 as shown in FIG. 7. Next, the first and second arms 16, 17 are gripped by hand and squeezed to produce pivotal movement of the first and second jaw portions 18, 19 into the closed positions shown in FIG. 8 and with the arm 17 engaging the stop 57. The resultant relative movement between the jaw portions 18 and 19 causes the head portion 45 of the insert 46 to compress the bias springs 49 and move the contact wedge portion 47 through the orifice 96 (FIG. 2) in the bottom wall 27 and the opening 75 in the top wall 61 of the cartridge 51 into the engagement cavity 76 as shown in FIG. 9. Forcible engagement between the contact wedge 47 and the end ferrule 78 produces bending thereof into a wedge shaped recess 98 in the lower wall 62 of the cartridge 51 as shown in FIG. 10. Consequently, the end ferrule 78 is securely crimped to the needle 101 so as to prevent withdrawal therefrom. To accommodate the crimping action, the wedge shaped recess 98 extends parallel to the axis of the contact wedge 47 and is aligned therewith.

Figure 11:
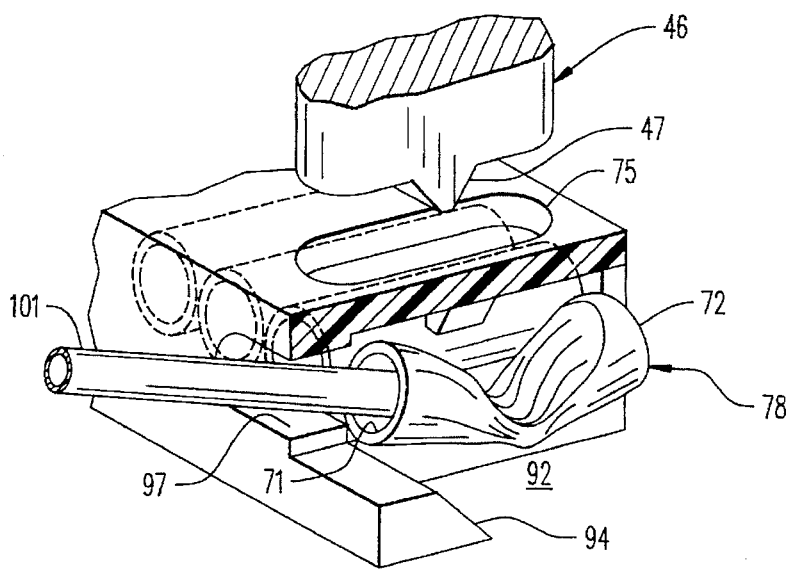
FIG. 11 is a perspective view illustrating a first step of removal of a crimped together needle and ferrule.

After the needle 101 and the end ferrule 78 have been crimped together, they are moved from the engagement cavity 76 into the removal cavity 92. During this movement of the crimped together needle 101 and ferrule 78, the outer exposed portion of the needle 101 passes through the removal passage or slot 30 (FIG. 7) in the funnel 29, the removal passage or slot 36 (FIG. 2) in the leg 24 of the first jaw 18 and the removal passage or slot 97 (FIG. 11) in the sidewall 64 of the cartridge 51. Also, movement of the ferrule 78 from the engagement cavity 76 into the removal cavity 92 is made possible by the downward depression 104 in the ferrule 78 created by the crimping action as shown in FIG. 10. The depression 104 provides clearance at the center portion of the ferrule 78 to permit passage by the centrally located abutment 91 on the top wall 61 of the cartridge 51. After having been displaced into the removal cavity 92, the crimped together needle 101 and ferrule 78 can be removed from the device 15 by withdrawal through the exit passage 35 (FIG. 12). Such removal is facilitated by the ramp surface 94 (FIG. 11) that guides movement of the ferrule 78 into the exit passage 35, the larger size of which accommodates withdrawal of the ferrule 58. Once removed from the device 15, the needle 101 can be disposed of safely in that the crimped on ferrule the 58 fully encapulates the needle's potentionally contaminated point.

As each crimped ferrule is displaced from the engagement cavity 76 into the removal cavity 92, the ferrule row 67 is moved inwardly by the spring member 87 to automatically and sequentially position each succeeding end ferrule 78 in the engagement cavity 76 in preparation for the insertion of another needle. Also, in the event that the arms 16 and 17 are activated to crimp an end ferrule 78 without a needle present in the engagement cavity 76, automatic ejection of the crimped ferrule into the removal cavity 92 prevents jamming of the device 15. After all of the ferrules 68 in a cartridge 51 have been exhausted, the tab 52 is forced downwardly, the cartridge 51 is removed through the open end 41 of the first arm 16 and a replacement cartridge is inserted.

Obviously, many modifications and variations of the present invention are possible in light of the above teachings. For example, although the device has been described in conjunction with disposal of hypodermic needles, the device 15 can be used in other applications in which it is desirable to encapsulate the exposed end of a shaft. It is to be understood, therefore, that the invention can be practiced otherwise than as specifically described.

What is claimed is:

1. A needle disposal device comprising:

first and second jaws; means defining an engagement chamber for retaining a ferrule and a removal cavity transversely juxtaposed thereto, said first and second jaws being reciprocably movable with respect to each other into and out of said engagement chamber;

entry means defining for a needle shaft an entry passage into said engagement chamber and axially aligned with the ferrule;

actuator means for producing relative closure movement between said first and second jaws into engagement with the ferrule in said engagement chamber so as to cause crimping thereof on the needle shaft;

exit means defining into said removal cavity an exit passage, said entry passage being of insufficient size to accommodate passage of said crimped ferrule and said exit passage being of sufficient size to accommodate passage of said crimped ferrules and means defining a removal passage extending between said entry passage and said exit passage and adapted to accommodate passage of the needle shaft during movement of the crimped ferrule between said engagement chamber and said removal cavity.

2. A device according to claim 1 wherein said crimping causes substantial distortion of the needle shaft into a dysfunctional shape.

3. A device according to claim 1 including bias means biasing said first and second jaws out of said engagement chamber and wherein said actuator means comprises a first arm extending from said first jaw and a second arm extending from said second jaw, said first and second arms adapted for manual actuation to produce relative pivotal movement of said first and second jaws into said engagement chamber.

4. A device according to claim 3 wherein said first and second arms are adapted to be gripped in a hand and squeezed thereby to produce said relative pivotal movement.

5. A device according to claim 4, further comprising retainer means for retaining a plurality of ferrules, said retainer means comprises housing means shaped and arranged to retain said ferrules in parallel engaged alignment within an elongated row having one end directly adjacent to said engagement chamber and an opposite end substantially spaced therefrom, said feed means comprises force means inducing on said row a force directed toward said engagement chamber; and including abutment means for engaging said individual ferrule within said engagement chamber so as to oppose said force induced by said force means.

6. A device according to claim 5 including stop means for limiting said relative movement of said first and second jaws in response to squeezing of said first and second arms.

7. A device according to claim 5 wherein said retainer means is a cartridge removably retained by said first arm, and said force means comprises a spring means exerting said force against said opposite end of said row of ferrules.

8. A device according to claim 7 wherein said cartridge defines an engagement cavity disposed within said engagement chamber adjacent to said one end of said row, an opening into said engagement cavity, and said abutment means that projects into said engagement cavity; and said second jaw defines a contact wedge portion adapted to enter said engagement cavity through said opening and engage said ferrule therein, said contact wedge having an axis extending transversely to said ferrule and substantially aligned with the mid-portion thereof.

9. A device according to claim 8 wherein said abutment means is aligned with the mid-portion of said ferrule and extends in a direction parallel thereto a distance substantially less than the length of said ferrule so as to accommodate passage of the crimped portion of the ferrule out of said engagement cavity.

10. A device according to claim 9 wherein said cartridge further defines a wedge shaped recess disposed in said engagement cavity opposite to said opening and having an axis substantially parallel to said axis of said contact wedge.

11. A device according to claim 10 wherein said first jaw further defines said entry passage which is axially aligned with said open end of said ferrule therein; an exit passage communicating with a portion of said engagement chamber separated from said engagement cavity by said abutment means; and a removal passage extending between said entry passage and said exit passage.

12. A device according to claim 11 wherein said entry passage is defined by a funnel having an inner end with dimensions smaller than those of said exit passage, and said removal passage comprises a longitudinal slot in said funnel.

13. A device according to claim 12 wherein said cartridge further defines a ramp portion adapted to guide movement of the crimped together shaft and ferrule through said exit passage.

14. A device according to claim 1 wherein said entry passage is defined by a funnel, and said means defining said removal passage comprise a longitudinal slot in said funnel.

15. A device according to claim 14 including ramp means for guiding movement of the crimped together shaft and ferrule through said exit passage, and wherein said funnel has an inner end with dimensions smaller than those of said exit passage.

16. A device according to claim 1 including abutment means disposed between said engagement chamber and said removal cavity, said abutment means being shaped and arranged to prevent movement of the ferrule from said engagement cavity into said removal chamber before crimping of the ferrule and to permit said movement thereof after crimping of the ferrule.

17. A ferrule applying device comprising:

first and second jaws defining an engagement chamber and reciprocably movable with respect to each other;

a retainer cartridge shaped and arranged to retain a plurality of ferrules in parallel engaged alignment within an elongated row; said retainer cartridge defining an engagement cavity disposed within said engagement chamber and adjacent to one end of the ferrule row, an opening into said engagement cavity, and an abutment means projecting into said engagement cavity;

entry means defining an entry passage shaped and arranged to allow insertion of a shaft into a ferrule positioned in said engagement cavity; and actuator means for producing relative closure movement between said first and second jaws into engagement with the ferrule in said engagement cavity so as to cause crimping thereof on the shaft, and wherein said second jaw defines a contact wedge portion adapted to enter said engagement cavity through said opening and engage the individual ferrule therein, said contact wedge having an axis extending transversely to the individual ferrule and substantially aligned with the mid-portion thereof, and said abutment means being aligned with the mid-portion of the ferrule and extending in a direction parallel thereto a distance substantially less than the length of the ferrule so as to accommodate passage of the crimped portion of the ferrule out of said engagement cavity.

18. A device according to claim 17 wherein said retainer cartridge further defines a wedge shaped recess disposed in said engagement cavity opposite to said opening and having an axis substantially parallel to said axis of said contact wedge.

19. A device according to claim 18 wherein said first jaw further defines said entry passage which is axially aligned with the ferrule; an exit passage communicating with a portion of said engagement chamber separated from said engagement cavity by said abutment means; and a removal passage extending between said entry passage and said exit passage.

* * * * *

UNITED STATES PATENT AND TRADEMARK OFFICE
CERTIFICATE OF CORRECTION

PATENT NO. : 5,623,762
DATED : April 29, 1997
INVENTOR(S) : Jennifer A. White

It is certified that error appears in the above-indentified patent and that said Letters Patent is hereby corrected as shown below:

Column 1, line 35, cancel "focussed" and substitute therefor --focused--.

Column 1, line 37, cancel "focussed" and substitute therefor --focused--.

Column 2, line 1, "Jaws" should read --jaws--.

Column 5, line 64, delete "the" (first occurrence).

Signed and Sealed this

Twenty-second Day of July, 1997

Attest:

Attesting Officer

BRUCE LEHMAN
Commissioner of Patents and Trademarks